United States Patent [19]

Schieder et al.

[11] 4,301,091
[45] Nov. 17, 1981

[54] FLUORESCENT DYESTUFFS

[75] Inventors: Rudolf Schieder, Huerth; Helmut Telle, Cologne; Roderich Raue, Leverkusen; Wolfgang Brinkwerth, Bergisch-Gladbach, all of Fed. Rep. of Germany

[73] Assignee: Bayer Aktiengesellschaft, Leverkusen, Fed. Rep. of Germany

[21] Appl. No.: 73,773

[22] Filed: Sep. 10, 1979

[30] Foreign Application Priority Data

Sep. 23, 1978 [DE] Fed. Rep. of Germany ....... 2841519

[51] Int. Cl.³ ..................... C07C 143/24; D06P 1/38
[52] U.S. Cl. ............................ 260/505 R; 260/456 P; 260/456 A; 260/465 R; 260/465 D; 260/465 H; 260/465 K; 260/465 G; 260/508; 260/509; 260/510; 260/512 C; 560/14; 8/648; 260/507 R
[58] Field of Search ........... 260/456 P, 505 C, 505 R, 260/456 A, 465 R, 465 D, 465 H, 465 K, 465 G, 507 C, 508, 509, 510, 512 C; 560/14

[56] References Cited

U.S. PATENT DOCUMENTS 3,822,305  7/1974  Pintschovius et al. ......... 260/505 C
4,013,713  3/1977  Weber et al. ................... 260/505 R Primary Examiner—Alan Siegel Attorney, Agent, or Firm—Sprung, Felfe, Horn, Lynch & Kramer

[57] ABSTRACT

Fluorescent dyestuffs of the formula

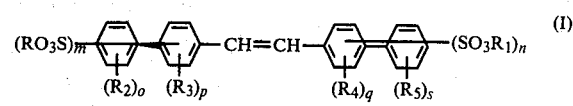

wherein:

$R_1$ and $R_2$ independently of one another represent hydrogen, a salt-forming cation, an alkyl radical with 1 to 8 carbon atoms or an aralkyl radical which is optionally substituted by non-chromophoric groups, $R_2$ to $R_5$ independently of one another represent hydrogen, alkyl, trifluoromethyl, alkoxy, aralkoxy, alkenyloxy, halogen or the carboxyl, cyano, alkylsulphonyl, arylsulphonyl, carboxamide or sulphonamide group or a carboxylic acid ester group, m and n independently of one another denote 0, 1 or 2 and the sum of m+n must be at least 2, and o, p, q and r independently of one another represent 0, 1 or 2.

processes for their preparation, their use for whitening organic materials and a process for the production of a coherent laser emission using the fluorescent dyestuffs according to formula I.

4 Claims, 4 Drawing Figures

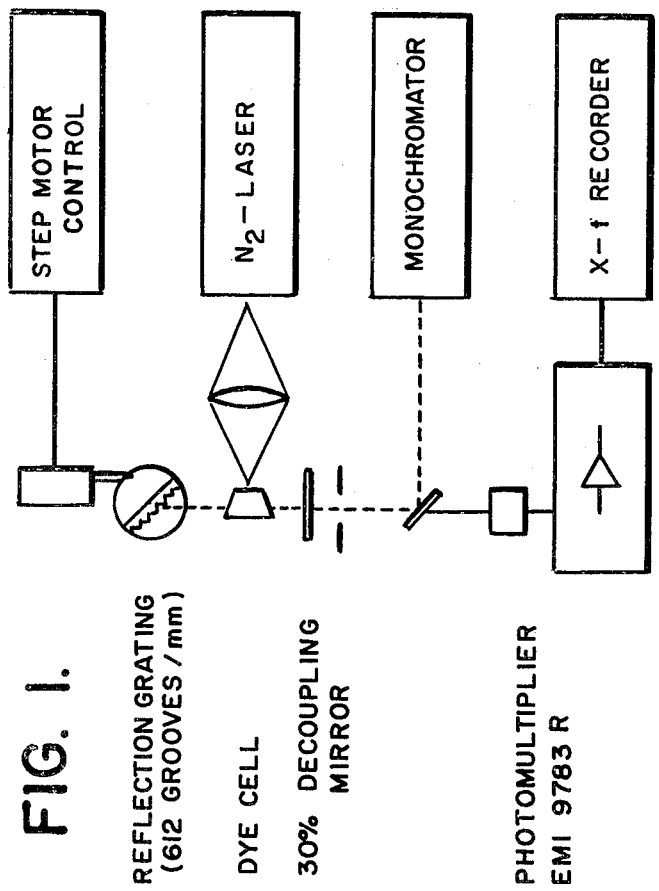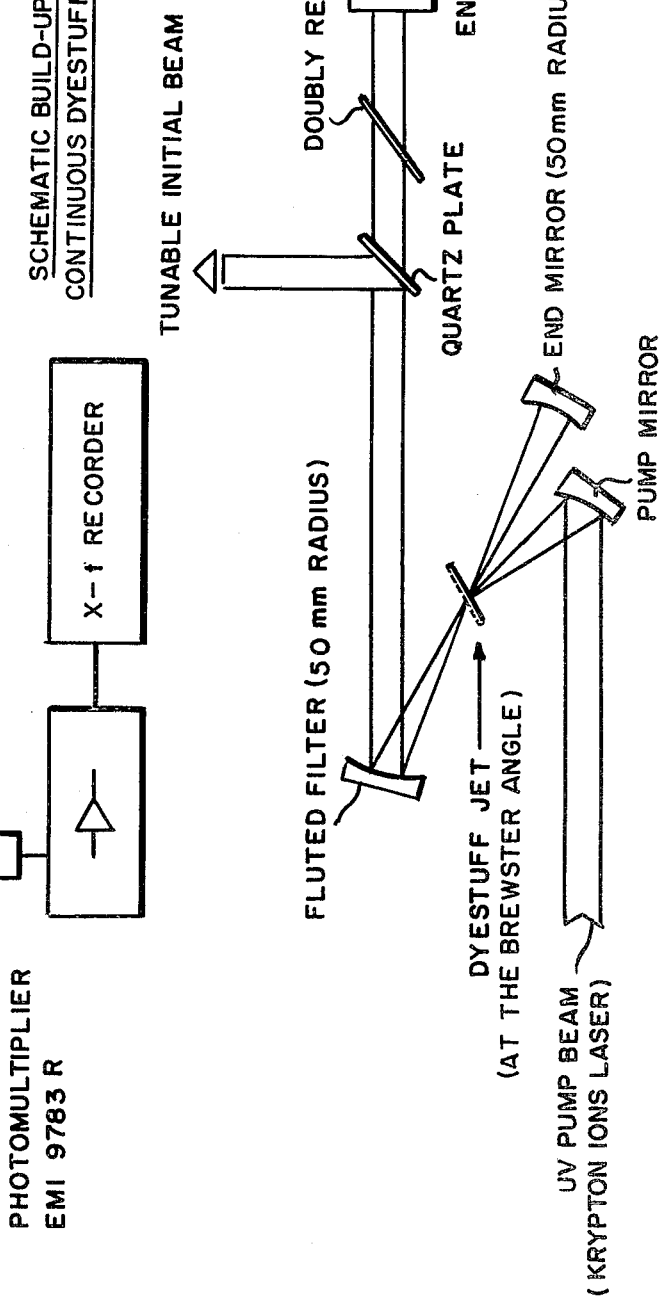

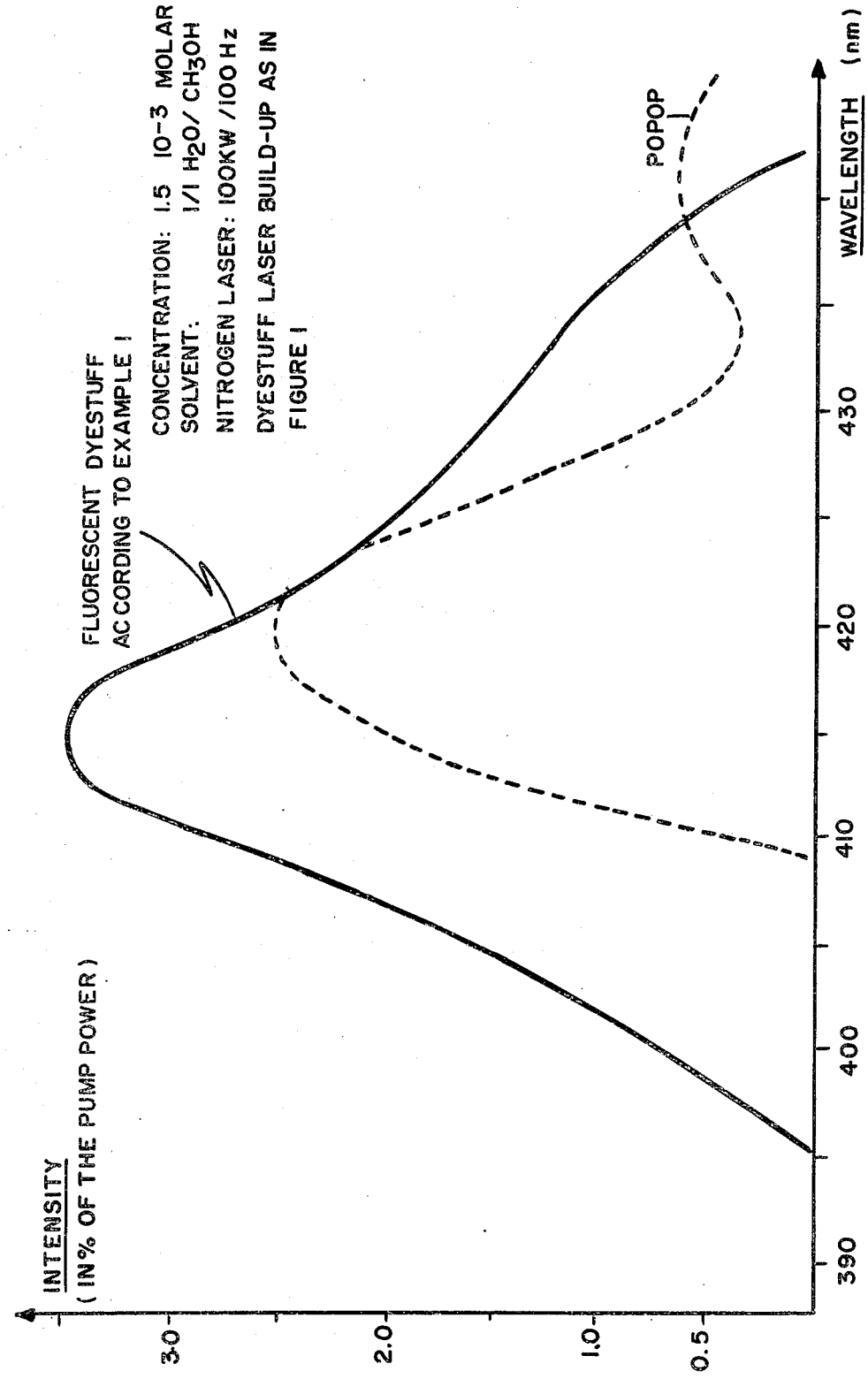

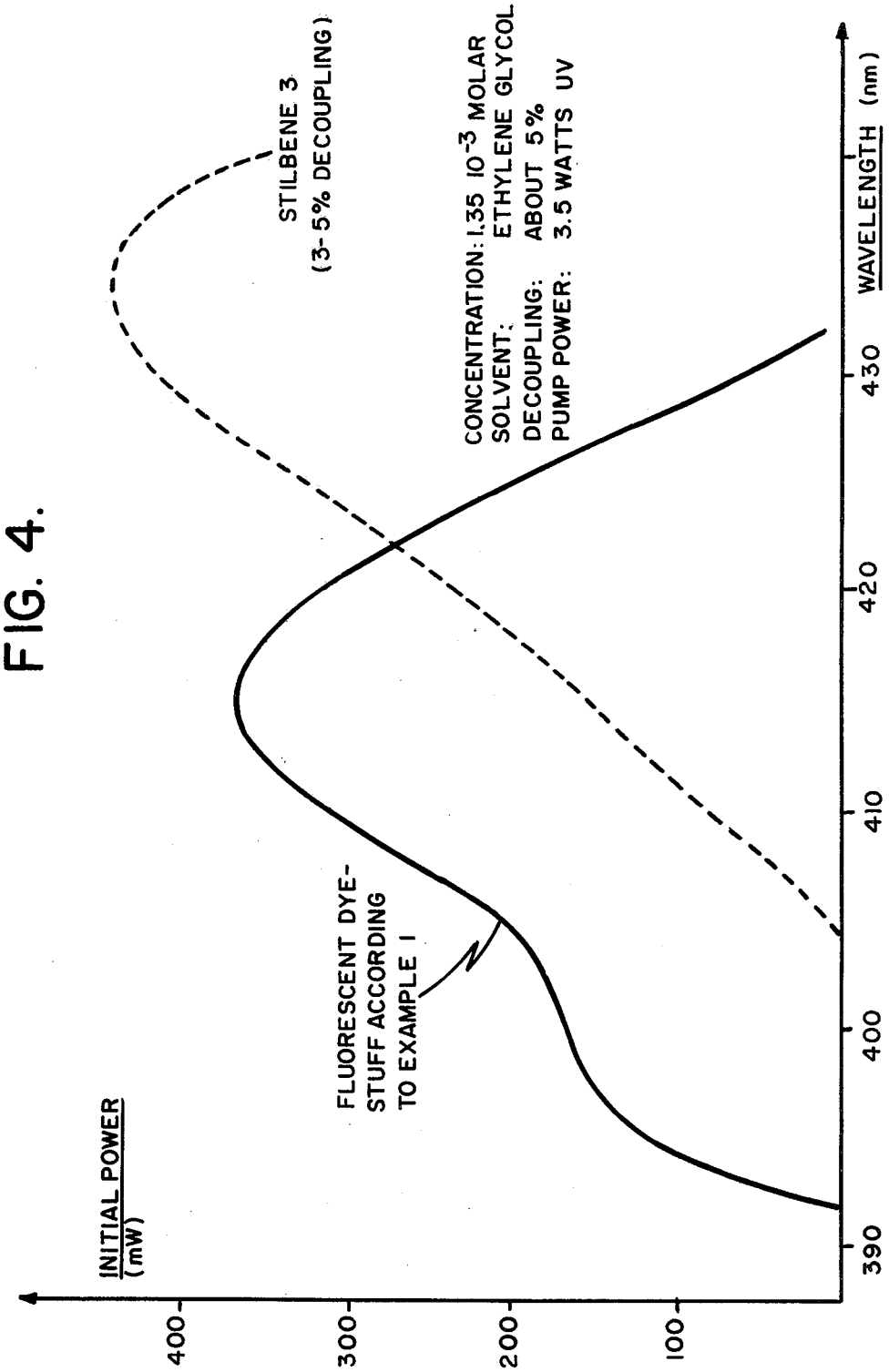

FLUORESCENT DYESTUFFS

The invention relates to fluorescent dyestuffs, processes for their preparation and their use for whitening organic materials and also as laser dyestuffs.

The new dyestuffs have the formula:

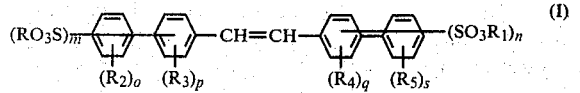

wherein

R and $R_1$ independently of one another represent hydrogen, a salt-forming cation, an alkyl radical with 1 to 8 carbon atoms or an aralkyl radical which is optionally substituted by non-chromophoric groups, $R_2$ to $R_5$ independently of one another represent hydrogen, alkyl, trifluoromethyl, alkoxy, aralkoxy, alkenyloxy, halogen, the carboxyl, cyano, alkylsulphonyl, arylsulphonyl, carboxamide or sulphonamide group or a carboxylic acid ester group, m and n independently of one another denote 0, 1 or 2 and the sum of m+n must be at least 2, and o, p, q and r independently of one another represent 0, 1 or 2.

Examples of substituents which may be mentioned are: $C_1$- to $C_5$-alkyl radicals, which can be further substituted by hydroxyl, cyano, halogen or phenyl, such as methyl, ethyl, cyanoethyl or tert.-butyl; benzyl; halogen atoms, such as chlorine, bromine or fluorine, preferably chlorine; $C_1$- to $C_5$-alkoxy radicals, such as methoxy, ethoxy, butoxy and isopropoxy; allyloxy; benzyloxy; $C_1$- to $C_5$-alkylsulphonyl radicals which are optionally substituted by hydroxyl, such as methylsulphonyl, ethylsulphonyl, n-butyl-sulphonyl and β-hydroxyethyl-sulphonyl; the benzylsulphonyl radical; the phenylsulphonyl radical; carboxamide or sulphonamide groups which are optionally nonosubstituted or disubstituted by $C_1$- to $C_4$-alkyl radicals; and also carboxylic acid $C_1$- to $C_4$-alkyl ester groups.

Possible salt-forming cations are monovalent or divalent metals, such as sodium, potassium, lithium, magnesium, calcium, barium, manganese and zinc; and also ammonium salts and their substitution products, which are obtained by reacting the acids on which they are based with mono-, di- or tri-methylamine, mono-, di- or tri-ethylamine, mono-, di- or tri-ethanolamine, methyldiethanolamine, ethyldiethanolamine, dimethylethanolamine, diethylethanolamine, mono-, di- or tri-isopropanolamine, methyldiisopropanolamine, ethyldiisopropanolamine, dimethylisopropanolamine, n-butylamine, sec.-butylamine, dibutylamine, diisobutylamine, triethoxyethanolamine, pyridine, morpholine or piperidine.

Preferred stilbene compounds have the formula:

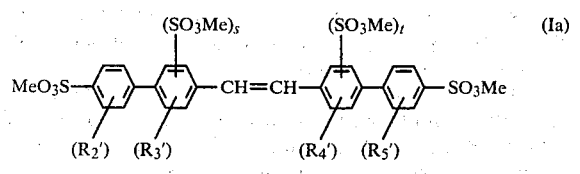

wherein

Me represents hydrogen, sodium, potassium or an optionally substituted ammonium radical, $R_2'$ to $R_5'$ independently of one another represent hydrogen, $C_1$- to $C_4$-alkyl, $C_2$- to $C_5$-alkoxyalkyl, benzyloxy, phenoxy, cyano, halogen or a carboxyl, carboxylic acid ester or carboxamide group and s and t denote 0 or 1.

A further preferred group has the formula:

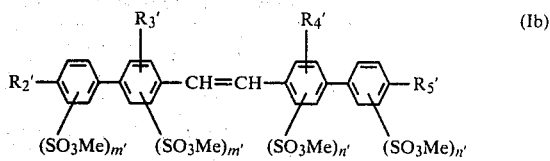

wherein

Me and $R_2'$ to $R_5'$ have the same meaning as in formula Ia and m' and n' represent 0 or 1 and the sum of m' and n' must be at least 2.

The compound of the formula

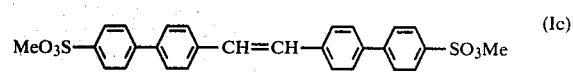

in which

Me has the same meaning as in formula Ia, is of particular importance for use as a laser dyestuff.

The stilbene compounds according to the invention can be prepared in a manner which is in itself known, by a condensation reaction of a compound of the formula

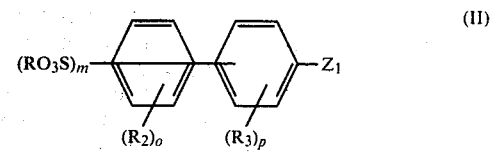

with a compound of the formula

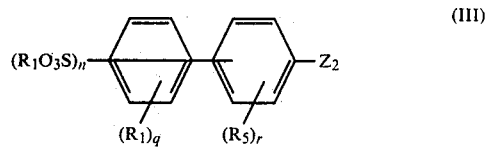

wherein the radicals R to $R_5$ and the indices m, n, o, p, q and r have the same meaning as in formula I and $Z_1$ and $Z_2$ reciprocally represent the aldehyde group or a radical of the formulae

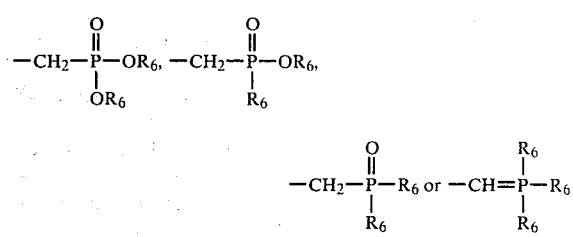

$R_6$=alkyl $C_{1-6}$, aryl, aralkyl or cycloalkyl in the presence of a strongly basic alkali metal compound and in the presence of a preferably hydrophilic, strongly polar solvent.

Examples of suitable solvents are toluene, xylene, chlorobenzene, alcohols, such as ethanol, and ethylene glycol monomethyl ether, but preferably N-methylpyrrolidone, dimethylformamide, diethylformamide, dimethylacetamide or dimethylsulphoxide.

The temperature at which the reaction is carried out can vary within wide limits. It is determined:

(a) by the stability of the solvent used towards the reactants, especially towards the strongly basic alkali metal compounds, (b) by the reactivity of the reactants taking part in the condensation reaction and (c) by the effectiveness of the solvent/base combination as a condensing agent.

The temperature is preferably approximately in the range from 30° C. to 60° C., but in many cases results which are already satisfactory can be obtained at room temperature (about 20° C.) on the one hand or, on the other hand, at temperatures of 100° C. and even at the boiling point of the solvent, if this is desired for reasons of a saving in time or in order to use a condensing agent which is less active but less expensive. In principle, reaction temperatures of 10° to 180° C. are thus also possible.

Strongly basic alkali metal compounds which can be used are, in particular, the hydroxides, amides and alcoholates (preferably those of primary alcohols containing 1 to 4 carbon atoms) of the alkali metals and for economic reasons those of lithium, sodium and potassium are of predominant interest. However, in principle and in special cases, alkali metal sulphides and alkali metal carbonates, arylalkali metal compounds, such as phenyl-lithium, or strongly basic amines (including ammonium bases, for example trialkylammonium hydroxides) can also be used successfully.

The phosphorus compounds of the formula II and III which are required as starting materials are obtained in a manner which is in itself known, by reacting halogenomethyl compounds, preferably chloromethyl or bromomethyl compounds of the formulae

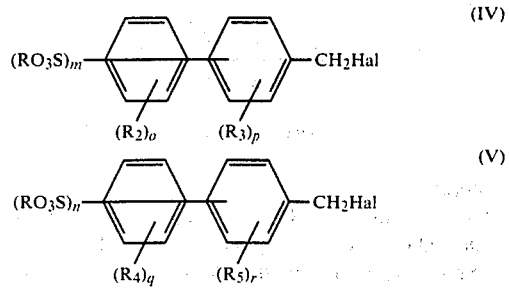

(IV)

(V)

in which the radicals R to $R_5$ and the indices m, n, o, p, q and r have the same meaning as in formula I and Hal represents chlorine or bromine, with phosphorus compounds of the formulae $(R_6O)_3P$, $R_6P(OR_6)_2$, $(R_6)_2POR_6$ or $P(R_6)_3$, in which $R_6$ has the meaning indicated above, $R_6$ radicals bonded to oxygen preferably being lower alkyl groups and $R_6$ radicals bonded directly to phosphorus, on the other hand, preferably being aryl radicals.

The halogenomethyl compounds of the formulae IV and V can be prepared from the corresponding methyl compound by the procedure described in German Pat. No. 234,913, by reaction with phosphorus pentachloride and chlorine and subsequent saponification of the sulphonyl chlorides, or by bromination with N-bromosuccinimide in accordance with the instructions of DOS (German Published Specification) No. 2,262,340. The bromomethyl group can also be introduced by reacting the corresponding diphenyl derivative with paraformaldehyde and sodium bromide in a sulphuric acid/glacial acetic acid mixture in accordance with the procedure described in DOS (German Published Specification) No. 2,262,340. A further route for the preparation of the halogenomethyl compounds of the formulae IV and V comprises the reduction of the biphenylaldehydesulphonic acids with sodium borohydride to give the hydroxymethylbiphenylsulphonic acids, conversion of the latter to the halogenomethylbiphenylsulphonyl chlorides with thionyl chloride or phosphorus pentachloride and subsequent esterification of the sulphonyl chlorides to the sulphonic acid esters.

Suitable halogenomethyl compounds of the formulae IV and V are: ethyl 4-chloromethylbiphenyl-4'-sulphonate, methyl 4-bromomethylbiphenyl-4'-sulphonate, ethyl 4-chloromethylbiphenyl-3-sulphonate, diethyl 4-chloromethylbiphenyl-3,4'-disulphonate, diethyl 4-bromomethyl-4'-methylbiphenyl-3,3'-disulphonate, 4-bromomethyl-4'-bromobiphenyl, 4-bromomethyl-4'-phenylsulphonylbiphenyl, 4-bromomethyl-4'-cyanobiphenyl and 4-bromomethyl-3'-methyl-4'-bromobiphenyl.

The aldehydes of the formulae II and III ($Z_1$ or $Z_2$=CHO) can be prepared from the halogenomethyl compounds by reaction with hexamethylenetetramine in acetic acid (Sommelet reaction). They are also obtained by postsulphonation of biphenyl-aldehydes with oleum in accordance with the procedure described in DOS (German Published Specification) No. 2,525,681. A further route to the biphenyl-aldehyde-sulphonic acids lies in the reaction of halogenated biphenyl-aldehydes with sodium sulphite.

Suitable biphenyl-aldehydes of the formulae II and III are: biphenyl-4-aldehyde-4'-sulphonic acid, biphenyl-4-aldehyde-3-sulphonic acid, biphenyl-4-aldehyde-3,4'-disulphonic acid, biphenyl-4-aldehyde, 3,4-dichlorobiphenyl-4'-aldehyde, 4-methylbiphenyl-4'-aldehyde-3,3'-disulphonic acid, 3-chlorobiphenyl-4'-aldehyde-4-sulphonic acid, 4-bromobiphenyl-4'-aldehyde, 4-cyanobiphenyl-4'-aldehyde and 3-methyl-4-bromobiphenyl-4'-aldehyde.

The compounds of the formula I can also be prepared by converting the substituents of a molecule which already has the basic structure of the compounds, to substituents which fall under the above definition of the formula I. Furthermore, in the compounds of the formula I, substituents can also be converted to other substituents which fall under the same definition.

In the dissolved or finely divided state, the compounds according to the invention display a more or less pronounced fluorescence. They can therefore be used for optically brightening synthetic or natural high molecular weight materials.

Synthetic organic high molecular weight materials are to be understood as meaning polymerisation, polycondensation and polyaddition products, as well as their after-treatment products, for example polymers based on $\alpha,\beta$-unsaturated carboxylic acids, dicarboxylic acids, carboxylic acid esters, amides, nitriles, olefine hydrocarbons, halogenated olefine hydrocarbons or olefine hydrocarbons containing aryl groups (such as polyethylene, polypropylene, polybutadiene, polyvinyl chloride, polyvinylidene chloride, polyacrylonitrile, polystyrene, polyacrylic acid derivatives and copolymers of two or more of the above-mentioned polymerisable monomers), polycondensation products based on bifunctional or polyfunctional compounds containing condensable groups and their homocondensation and co-condensation products (such as polyesters, polyamides, maleate resins, polycarbonates, silicone resins, phenol/formaldehyde or melamine/formaldehyde resins and others), polyaddition products, such as cross-linked or uncrosslinked polyurethanes, and epoxide resins.

Semi-synthetic organic materials which may be mentioned are, for example, cellulose esters and cellulose ethers, nitrocellulose, regenerated cellulose and plastics based on casein.

Natural high molecular weight organic materials which can be optically brightened are, for example, protein materials, such as wool, silk and leather; cellulose materials, such as cotton, paper and wood pulps in a state of fine division; and also rubber, gutta percha or balata.

The organic materials to be optically brightened can be in very diverse stages of processing, in the form of raw materials, semi-finished goods or finished goods, for example in the form of powders, chips, granules, foams, lacquers, dispersions, mouldings, such as, for example, thin or thick sheets and films, tapes, filaments, fibres, for example in the form of continuous filaments, staple fibres, flocks, yarns, hank goods, twisted yarns, long-wovens, felts, waddings and textile woven fabrics, composite materials and knitted fabrics, and also in the form of putties, pastes, waxes, adhesives and trowelling compositions and the like.

The compounds according to the invention are preferably used for the optical brightening of fibre materials and plastics. The compounds according to the invention which are anionically soluble in water are particularly suitable for the optical brightening of natural and regenerated cellulose fibres and of wool and synthetic polyamide fibres.

Particularly good brightening effects are sometimes also obtained when the compounds according to the invention are combined with other optical brighteners. Combinations of this type are of interest especially when it is desired to obtain alterations in the shade with the brightening effect.

The compounds, according to the invention, of the general formula I can also be added to detergents which contain the customary fillers and auxiliaries. They are distinguished, in particular, by the fact that they can be employed in the presence of oxidative and reductive bleaching agents, for example hydrogen peroxide, sodium hypochlorite and sodium chlorite, without impairing the optical brightening effect.

Solutions of the compounds of the formula I are also suitable for the production of coherent monochromatic radiation (laser light), the frequency of which can be changed, by means of a dyestuff laser which consists of a reservoir for the dyestuff solution and an energy source, associated therewith, which is capable of exciting the dyestuff solution to produce an emission, the radiation produced being in the wavelength range of 390 to 440 nm.

A laser is a light intensification device by means of which it is possible to produce coherent monochromatic light of a high spectral and geometric intensity density. The laser consists of an optical resonator which contains the liquid laser-active material in a thin-walled quartz cell. The cell is usually part of a closed system through which the dyestuff solution is circulated by pumping whilst the laser is in operation. The active medium can also be in the form of a liquid jet, which issues from a nozzle vertically to the optical axis and transverses the resonator. Local overheating, which would lead to optical inhomogeneities, is avoided in both arrangements.

The excitation of the dyestuffs is effected with the aid of energy sources, by means of electrons or light, and the dyestuff laser can also be excited by a gas laser, for example a nitrogen laser, argon laser or krypton laser.

The excitation, which is also termed optical pumping, has the effect of raising the electrons of the molecule of the laser dyestuff from their normal state to a high energy state, from which a radiation transition takes place. If the number of molecules present in the excited state exceeds that of the molecules in lower states, this gives rise to stimulated transitions, by means of which the light is intensified in the optical resonator.

If one of the laser mirrors is partially transparent to light, a part of the radiation leaves the apparatus in the form of a laser beam. Dyestuffs which can be excited particularly easily exhibit the phenomenon of super radiance with highly effective excitation. This can be observed, for example, if a quartz cell containing the solution of such a dyestuff is placed in the beam of a nitrogen laser. The solution then emits light in a preferred direction, similarly to the case of a laser, without being located between resonator mirrors.

A considerable advantage of the dyestuff laser compared with solid or gas lasers is its ability to supply laser radiation of a frequency which can be changed. Because of the width of the fluorescence band of the dyestuffs employed, dyestuff lasers can be so tuned, by inserting a frequency-selective element, for example a reflection grating, prism or doubly refracting filter, that laser light is emitted at any desired wavelength within the entire fluorescence band of the dyestuff.

Although a large number of suitable dyestuffs has already been proposed, there is, nevertheless, still a considerable lack in many regions of the visible wavelength range and above all in the near UV of compounds which give a very high degree of effectiveness of the laser. Moreover, it has not been possible hitherto to produce continuous laser radiation below 410 nm. When used in dyestuff lasers, the compounds according to the invention are distinguished by an exceptionally high stability to light.

In recent years laser light from lasers which have a frequency which can be changed has attained considerable importance in spectroscopy. The lasers can be employed for analytical purposes, high resolution spectroscopy, fluorescence spectroscopy, absorption spectroscopy, life measurements and photoionisation and in the spectroscopy of negative ions. They are also of great technical importance in information techniques, in environmental protection and for the separation of isotopes.

BRIEF DESCRIPTION OF DRAWINGS

Referring to the drawings appended hereto,

FIG. 1 is a schematic diagram of an apparatus used for the generation of a wave-length by use of the fluorescent dyestuff of the invention;

FIG. 2 is a graph showing the dependence of the laser power on the wave length for dyestuff of the invention and for a known laser dyestuff, POPOP (1,4-bis-[2-5-phenyloxazolyl)]-benzene);

FIG. 3 is a schematic diagram showing an arrangement of lenses, a source of UV light which in connection with a reservoir for a fluorescent dyestuff is employed for the build-up of continuous dyestuff laser; and FIG. 4 is a graph similar to that of FIG. 2, showing the dependence of the laser power on the wave-length when the same is generated in accordance with Example 5 of the application.

EXAMPLE 1

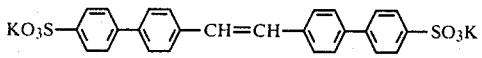

40.0 g of potassium tert.-butylate (about 90% pure) are suspended in 300 ml of dimethylformamide (anhydrous) in a reaction vessel, with the exclusion of moisture and atmospheric oxygen. At a reaction temperature of 40°–50° C., a filtered solution of 40 g of potassium biphenyl-4-aldehyde-4'-sulphonate (about 80% pure) in 1,100 ml of dimethylformamide, which has been stirred with a solution of 68 g of ethyl 4-diethoxyphosphonomethylbiphenyl-4'-sulphonate in 100 ml of dimethylformamide, is added dropwise in the course of 1 hour. The reaction mixture is stirred for 2 hours at 40°–50° C. until no further starting compounds can be detected in a thin layer chromatogram. With the addition of 300 ml of water, the reaction mixture is heated at 80°–90° C. for about 2 hours until it is colourless. After cooling and filtering and washing the product with a little water and drying in vacuo at 80° C., the compound of the formula indicated above is obtained in the form of a colourless crystalline product. Yield: 56.8 g = 62.5% of theory.

To convert the product to the more readily soluble ammonium salts, the potassium salt is heated with half-concentrated ammonia solution, with triethanolamine or with tris-2-hydroxyethoxyethylamine.

The potassium biphenyl-4-aldehyde-4'-sulphonate used as the starting material was obtained in the following way:

182 g of biphenyl-4-aldehyde are introduced in portions into 400 g of 20% strength oleum at a rate such that the temperature slowly rises from 25° C. to 50° C. The temperature is kept at 50° C. for 3 hours and the reaction mixture is then discharged onto 1,000 g of ice and 30 g of potassium chloride. Potassium biphenyl-4-aldehyde-4'-sulphonate precipitates as a flocculent precipitate. The crude product is recrystallised from water with the addition of active charcoal. Yield: 258.3 g = 85% of theory.

The ethyl 4-diethoxyphosphonomethylbiphenyl-4'-sulphonate used as a starting material was prepared in the following way:

1st stage: 4-Hydroxymethylbiphenyl-4'-sulphonic acid 166 g of potassium biphenyl-4-aldehyde-4'-sulphonate (80% pure) are suspended in 600 ml of water and 100 ml of 10% strength sodium hydroxide solution are added. A solution of 6.2 g of sodium borohydride in 300 ml of water and 30 ml of 10% strength sodium hydroxide solution is added in portions, under nitrogen. The temperature rises to 30° C., with vigorous evolution of hydrogen. The reaction mixture is stirred at room temperature for 14 hours. After the reduction is complete, the mixture is carefully acidified with concentrated hydrochloric acid and the suspension is heated at 80° C. for 3 hours in order to destroy the boron complex and to form the acid. After cooling, the 4-hydroxymethyl biphenyl-4'-sulphonic acid is filtered off, washed with little water and dried in vacuo at 100° C. Yield: 11 g = 93% of theory.

2nd stage: 4-Chloromethylbiphenyl-4'-sulphonyl chloride 113 g of 4-hydroxymethylbiphenyl-4'-sulphonic acid are suspended in 800 ml of chlorobenzene and 250 ml of chlorobenzene are distilled off in order to remove the water completely. The suspension is then cooled to 80°–90° C. and, after adding 3 ml of dimethylformamide and 1 g of phosphorus pentachloride, 150 ml of thionyl chloride are added dropwise in the course of 2 hours. The temperature is kept at 85°–95° C. for 14 hours. The solvent and excess thionyl chloride are distilled off in vacuo, virtually to dryness. The residue is extracted hot with 900 ml of methylcyclohexane, salts and unconverted sulphonic acid remaining as a residue, whilst the sulphonyl chloride separates out from methylcyclohexane on cooling as a colourless crystalline compound. Yield: 100.6 g = 78% of theory. Melting point 110°–112° C.

3rd stage: Ethyl 4-chloromethylbiphenyl-4'-sulphonate 98 g of 4-chloromethylbiphenyl-4'-sulphonyl chloride are dissolved in 400 ml of tetrahydrofurane (anhydrous), with the exclusion of moisture and oxygen, and a 10% excess of sodium alcoholate, prepared from 8 g of sodium and 1,000 ml of absolute alcohol, is added in portions, so that the reaction temperature is kept at 10°–15° C. with ice-cooling. After stirring at room temperature for one hour, the solvent mixture is stripped off in vacuo at 50° C. The residue is extracted hot with 1,200 ml of di-sec.-butyl ether (anhydrous). After cooling and filtering and drying the product in vacuo at 50° C., 68.5 g of ethyl 4-chloromethylbiphenyl-4'-sulphonate are obtained. Yield: 68%. Melting point: 112°–116° C.

4th stage: Ethyl 4-diethoxyphosphonomethylbiphenyl-4'-sulphonate 48.5 g of ethyl 4-chloromethylbiphenyl-4'-sulphonate are suspended in 100 ml of anhydrous xylene, with the exclusion of moisture and oxygen. Starting at a temperature of 130°–140° C., 75 g of triethyl phosphite are added dropwise in the course of 2 hours, whilst distilling off the resulting ethyl chloride and xylene and triethyl phosphite at the same time, the rate of addition being such that the temperature slowly rises to 165°–170° C. The reaction mixture is kept at this temperature for 7 hours. Excess triethyl phosphite is distilled off at 160° C. and 20 mbars. The crude oil (68 g) which remains as the residue is taken up in 100 ml of dimethylformamide and in this form is reacted with potassium biphenyl-4-aldehyde-4'-sulphonate.

EXAMPLE 2

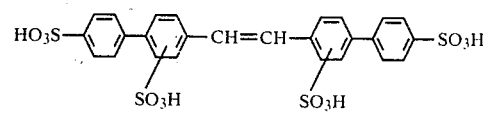

10 g of the compound prepared according to Example 1 are introduced into 50 ml of 20% strength oleum at 0°–10° C. and the mixture is stirred at 5° C. for 30 minutes. The temperature is raised to 25° C. in the course of 1 hour. After discharging onto a mixture of ice and water, the mixture is neutralised with calcium hydroxide and the resulting calcium sulphate is filtered off and washed thoroughly with water. The filtrate is clarified with active charcoal and the calcium salt is converted to the free sulphonic acid on a strongly acid ion exchanger.

The diphenylstilbenesulphonic acids of the formula

A—CH=CH—A' listed in the table which follows can be prepared in a manner similar to that described in the above examples.

| A | A' |
|---|---|
| KO₃S–⟨⟩–⟨⟩– | –⟨⟩–⟨⟩ (SO₃K) |
| KO₃S–⟨⟩–⟨⟩– | –⟨⟩–⟨⟩–SO₃K (SO₃K) |
| KO₃S–⟨⟩–⟨⟩– | –⟨⟩–⟨⟩–CH₃ (SO₃K, SO₃K) |
| KO₃S–⟨⟩–⟨⟩– (Cl) | –⟨⟩–⟨⟩–SO₃K (Cl) |
| KO₃S–⟨⟩–⟨⟩– (SO₃K) | –⟨⟩–⟨⟩–SO₃K (SO₃K) |
| KO₃S–⟨⟩–⟨⟩– (SO₃K) | –⟨⟩–⟨⟩–CH₃ (SO₃K, SO₃K) |
| KO₃S–⟨⟩–⟨⟩– (SO₃K) | –⟨⟩–⟨⟩–SO₃K (Cl) |
| CH₃–⟨⟩–⟨⟩– (SO₃K, SO₃K) | –⟨⟩–⟨⟩–CH₃ (SO₃K, SO₃K) |
| CH₃–⟨⟩–⟨⟩– (SO₃K, SO₃K) | –⟨⟩–⟨⟩–Br |
| CH₃–⟨⟩–⟨⟩– (SO₃K, SO₃K) | –⟨⟩–⟨⟩–Br (CH₃) |
| CH₃–⟨⟩–⟨⟩– (SO₃K, SO₃K) | –⟨⟩–⟨⟩–Cl (Cl) |
| CH₃–⟨⟩–⟨⟩– (SO₃K, SO₃K) | –⟨⟩–⟨⟩–CN |
| CH₃–⟨⟩–⟨⟩– (SO₃K, SO₃K) | –⟨⟩–⟨⟩–COOH |
| CH₃–⟨⟩–⟨⟩– (SO₃K, SO₃K) | –⟨⟩–⟨⟩ |
| CH₃–⟨⟩–⟨⟩– (SO₃K, SO₃K) | –⟨⟩–⟨⟩–SO₂–⟨⟩ |
| KO₃S–⟨⟩–⟨⟩– (SO₃K) | –⟨⟩–⟨⟩ |
| KO₃S–⟨⟩–⟨⟩– (SO₃K) | –⟨⟩–⟨⟩–Br |
| KO₃S–⟨⟩–⟨⟩– (SO₃K) | –⟨⟩–⟨⟩–Br (CH₃) |
| KO₃S–⟨⟩–⟨⟩– (SO₃K) | –⟨⟩–⟨⟩–Cl (Cl) |
| KO₃S–⟨⟩–⟨⟩– (SO₃K) | –⟨⟩–⟨⟩–CN |
| KO₃S–⟨⟩–⟨⟩– (SO₃K) | –⟨⟩–⟨⟩–COOH |
| KO₃S–⟨⟩–⟨⟩– (SO₃K) | –⟨⟩–⟨⟩–SO₂–⟨⟩ |
| KO₃S–⟨⟩–⟨⟩– | –⟨⟩–⟨⟩–SO₂–⟨⟩ |

EXAMPLE 3

Using a liquor ratio of 1/40, a polyamide fibre fabric is introduced at 60° C. into a bath which contains, based on the weight of material, 0.1% of the brightener described in Example 2 and also, per liter, 1 g of 80% strength acetic acid and 0.25 g of an adduct of 30–35 mols of ethylene oxide with 1 mol of technical grade stearyl alcohol. The mixture is heated to the boil in the course of 30 minutes and kept at the boil for 30 minutes. After rinsing and drying, the polyamide fabric displays a good brightening effect.

EXAMPLE 4

The compound prepared in accordance with the instructions of Example 1 was dissolved in a concentration of $1.5 \times 10^{-3}$ mol/l in a mixture of 50% of methanol and 50% of water. In an apparatus according to FIG. 1, this solution was pumped from a reservoir through the dyestuff cell. The frequency of the wavelength was varied by a reflection grating with a step motor drive. The laser spectrum was recorded via a photomultiplier, which was spectrally calibrated, and the wavelength was calibrated via a monochromator. In order to measure the power, the photomultiplier was replaced by a thermopile measuring head with an ancillary measuring amplifier. The intensity in percent of the pump is also given in kW since the initial pulse power was 100 kW.

The nitrogen laser used had a wavelength of 337 mm, a pulse frequency of 100 Hz, a pulse width of 7 nseconds and a pulse peak power of 100 kW.

The dependence of the laser power on the wavelength is given in FIG. 2. The known laser dyestuff POPOP (1,4-bis-[2-(5-phenyloxazolyl)]-benzene), the laser activity of which is described in Optics Communications 24, 1—page 33 (Jan. 1978), was used as the comparison substance. The compound according to the invention shows a higher initial power over a wider spectral range.

EXAMPLE 5

The fluorescent dyestuff prepared in accordance with the instructions of Example 1 was dissolved in a concentration of $1.35 \times 10^{-3}$ mol/l in ethylene glycol. In a dyestuff laser arrangement according to FIG. 3, this solution was introduced by means of a jet from a nozzle into the laser resonator. The krypton laser used as the pump laser for continuous excitation had a wavelength of 351/356 nm and a maximum initial power of 3.5 W. The frequency of the wavelength was varied by a doubly refracting filter. The effective power was decoupled by means of a quartz plate which was inserted in the laser resonator at a suitable angle. The laser spectrum was recorded in point form by rotating the frequency-selective doubly refracting filter and the initial power at a set wavelength was determined using a thermopile power meter. The initial power is given in mW.

The dependence of the laser power on the wavelength is shown in FIG. 4. Stilbene 3, the laser activity of which is described in Optics Communications 24, 3—page 251 (Mar. 1978), is used as the comparison dyestuff. The compound according to the invention displays a higher initial power over a spectral range which is considerably extended towards the near UV. The category of dyestuffs according to the invention thus permits a cw operation in the spectral range below 400 nm for the first time.

Similarly good results are obtained when fluorescent dyestuffs which have the formulae listed at the end of Example 2 are employed in place of the compound indicated above.

We claim:
1. Fluorescent dyestuffs of the formula

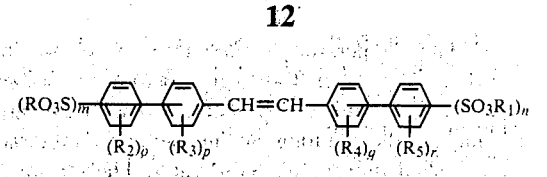

wherein
R and $R_1$ independently of one another represent hydrogen, a salt-forming cation, an alkyl radical with 1 to 8 carbon atoms or an aralkyl radical which is optionally substituted by non-chromophoric groups,
$R_2$ to $R_5$ independently of one another represent hydrogen, alkyl, trifluoromethyl, alkoxy, aralkoxy, alkenyloxy, halogen, the carboxyl, cyano, alkylsulphonyl, arylsulphonyl, carboxamide or sulphonamide group or a carboxylic acid ester group, m and n independently of one another denote 0, 1 or 2 and the sum of m+n must be at least 2, and o, p, q and r independently of one another represent 0, 1 or 2.
2. Fluorescent dyestuffs of the formula

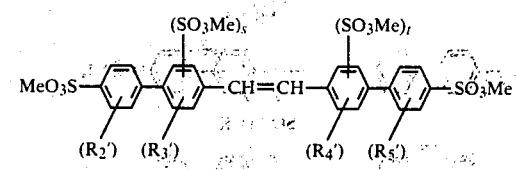

wherein
Me represents hydrogen, sodium, potassium or an optionally substituted ammonium radical,
$R_2'$ to $R_5'$ independently of one another represent hydrogen, $C_1$- to $C_4$-alkyl, $C_2$- to $C_5$-alkoxyalkyl, benzyloxy, phenoxy, cyano, halogen or a carboxyl, carboxylic acid ester or carboxamide group and s and t denote 0 or 1.
3. Fluorescent dyestuffs of the formula

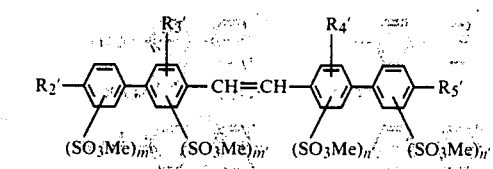

wherein
Me and $R_2'$ to $R_5'$ have the same meaning as in claim 2 and
m' and n' represent 0 or 1 and the sum of m' and n' must be at least 2.
4. A fluorescent dyestuff of the formula

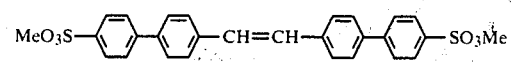

in which
Me has the same meaning as in claim 2.

* * * * *